United States Patent [19]

Nagel et al.

[11] Patent Number: 5,395,405
[45] Date of Patent: Mar. 7, 1995

[54] METHOD FOR PRODUCING HYDROCARBON GAS FROM WASTE

[75] Inventors: Christopher J. Nagel, Wayland; Thomas P. Griffin, Norton, both of Mass.

[73] Assignee: Molten Metal Technology, Inc., Waltham, Mass.

[21] Appl. No.: 46,693

[22] Filed: Apr. 12, 1993

[51] Int. Cl.⁶ .............................. C10J 3/00; C07C 4/04
[52] U.S. Cl. ................................... 48/197 R; 48/92; 585/240
[58] Field of Search ............... 48/92, 197 R, 197 A; 110/346; 423/210.5, DIG. 12; 585/240; 588/201, 205, 226

[56] References Cited

U.S. PATENT DOCUMENTS

| | | | |
|---|---|---|---|
| 3,542,352 | 11/1970 | Thermelis | 266/36 |
| 3,642,583 | 2/1972 | Greenberg et al. | 203/11 |
| 3,668,120 | 6/1972 | Patterson | 48/92 X |
| 3,812,620 | 5/1974 | Titus et al. | 48/111 X |
| 4,012,457 | 3/1977 | Bredeson et al. | 385/635 |
| 4,085,923 | 4/1978 | Queneau et al. | 266/215 |
| 4,511,372 | 4/1985 | Axelsson | 48/197 R |
| 4,574,714 | 3/1986 | Bach et al. | 110/346 |
| 4,602,574 | 7/1986 | Bach et al. | 110/346 |
| 4,666,696 | 5/1987 | Shultz | 423/659 |
| 4,925,537 | 5/1990 | Meuser et al. | 202/219 |
| 5,117,304 | 5/1992 | Nagel | 588/201 |
| 5,136,117 | 8/1992 | Paisley et al. | 585/241 |
| 5,139,558 | 8/1992 | Lauwers | 65/135 |
| 5,139,568 | 9/1992 | Geiger | 75/501 |

FOREIGN PATENT DOCUMENTS

WO92/12265  7/1992  WIPO .

OTHER PUBLICATIONS

Paisley, M. A., "Development Opportunity Ethylene Recovery From Waste Plastics", (Dec. 11, 1992).

*Primary Examiner*—Robert J. Warden
*Assistant Examiner*—Robert Carpenter
*Attorney, Agent, or Firm*—Hamilton, Brook, Smith & Raynolds

[57] ABSTRACT

A method for dissociating organic waste to produce a gasified hydrocarbon. The method of the invention includes directing an organic waste, into a reaction zone containing a molten metal bath in a reactor maintained under conditions sufficient to dissociate the organic waste and to form a gasified hydrocarbon component. Wherein the organic waste includes an inorganic component, the an inorganic component is retained in a vitreous and/or molten metal phase or is removed form the gaseous phase by physical or chemical separation.

14 Claims, 1 Drawing Sheet

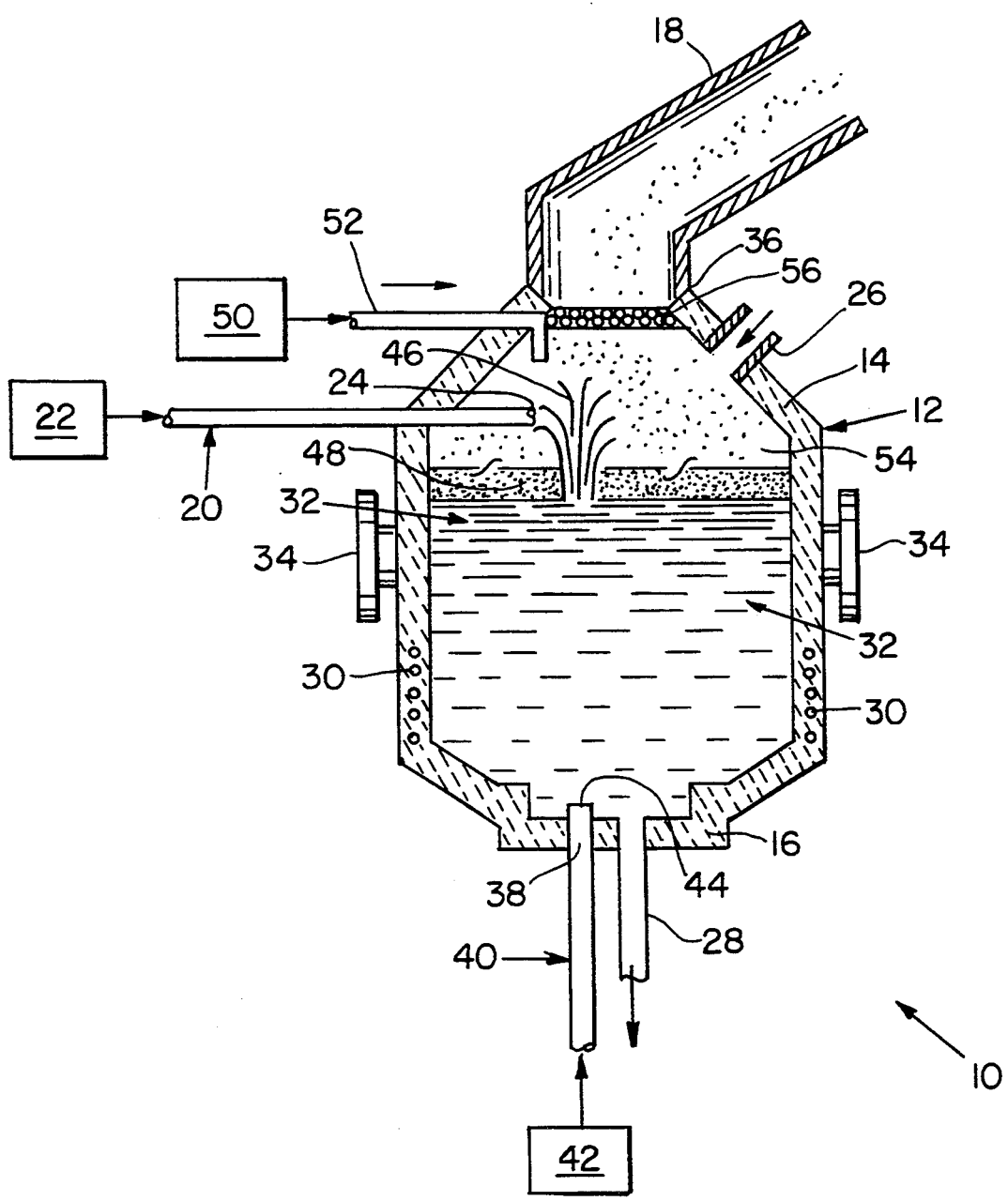

METHOD FOR PRODUCING HYDROCARBON GAS FROM WASTE

BACKGROUND OF THE INVENTION

Many organic wastes are produced every year, including organic wastes which contain organically and inorganically bound inorganic contaminants such as metals, silicates, halogens and sulfur, or organic wastes which are hazardous or toxic. The hydrocarbons in these organic wastes could be potential sources of highly caloric carbon compounds which could be utilized as chemical or energy resources. Such wastes include organic and organometallic materials. Examples of such organic wastes include plastics, polymers, coke wastes, petroleum residuals, tires, and pesticides.

Currently, many of these organic wastes are disposed in landfills or by incineration. However, disposal of organic wastes in landfills and by incineration has become an increasingly difficult problem because of diminishing availability of disposal space, strengthened governmental regulations, and the growing public awareness of the impact of the disposal of hazardous and non-hazardous waste upon the environment. Release of organic wastes to the environment can contaminate air and water supplies thereby diminishing the quality of life in the affected populations.

Furthermore, disposal of these organic wastes without producing valuable products or reclaiming valuable components constitutes an economic loss of valuable chemical resources.

To minimize the environment and economic effects associated with the disposal of organic wastes, methods must be developed to convert these organic wastes into useful and benign substances.

SUMMARY OF THE INVENTION

The present invention relates to a method for producing a hydrocarbon from an organic waste. In another embodiment of the invention, the organic waste contains an inorganic compound.

The method of the invention involves forming a reaction zone, containing a molten metal bath, in a reactor and maintaining the reaction zone under conditions sufficient to dissociate the organic waste to form a gasified hydrocarbon. The organic waste is then introduced into the reaction zone whereby the organic waste dissociates to form the desired gasified hydrocarbon.

This invention has the advantage of generating highly caloric gaseous carbon compounds, such as hydrocarbons, which can be useful as chemical or energy resources from an organic waste.

An additional advantage of this invention is that it can provide a method for processing waste of diverse chemical natures to produce usable hydrocarbons while permitting the recovering of metals, and metal compounds, such as metal oxides, metal phosphates and metal sulfides, from organic wastes containing inorganic impurities.

BRIEF DESCRIPTION OF THE DRAWING

The Figure is a cut-away side elevational illustration of an apparatus suitable for producing a hydrocarbon in a reaction zone, containing a molten metal bath, from an organic waste.

DETAILED DESCRIPTION OF THE INVENTION

The features and other details of the method and apparatus of the invention will now be more particularly described with reference to the accompanying drawing and pointed out in the claims. It will be understood that the particular embodiments of the invention are shown by way of illustration and not as limitations of the invention. The principle features of this invention can be employed in various embodiments without departing from the scope of the present invention.

The method of this invention employs a molten metal bath for destroying waste by dissociating the waste to form various products, such as the Bach/Nagel method disclosed in U.S. Pat. Nos. 4,574,714 and 4,607,574. The teachings of U.S. Pat. Nos. 4,574,714 and 4,607,574 are incorporated herein by reference.

One embodiment of the present invention is illustrated in FIG. 1. Apparatus 10 includes reactor 12. Examples of suitable reactors, fitted with appropriate injection means include "T"-shaped reactors, top and bottom-blown basic oxygen process reactors (K-BOP and Q-BOP, respectively), argon-oxygen decarbonization furnaces, electric arc furnaces, which have been fitted with a suitable means for charging or injection through the top, bottom or sides of the reactor, such as is known in conventional steel-making practices. Reactor 12 includes upper portion 14 and lower portion 16. Off-gas outlet 18, which extends from upper portion 14, is suitable for conducting a gasified hydrocarbon out of reactor 12. Suitable organic waste introduction means, such as lance 20, which can be consumable, is disposed at upper portion 14 of reactor 12. Lance 20 provides fluid communication between organic waste source 22 and upper portion 14 of reactor 12 through waste inlet 24. Waste inlet 24 is disposed in upper portion 14 of reactor 12 at the end of lance 20.

In another embodiment, a second suitable organic waste introduction means, such as bulk waste inlet 26, extends from upper portion 14 of reactor 12. Bulk waste inlet 26 provides a means for directing bulky organic waste into reactor 12.

It is understood that suitable means for introducing organic waste into reactor 12 includes tuyeres, lances, inlets and other components capable of directing organic waste into the reactor. Additionally, means for introducing organic waste can direct the organic waste into upper portion 14 or lower portion 16 of reactor 12. It is also understood that the means of introducing organic waste can direct organic waste into reactor 12 through the top, bottom or sides of reactor 12. Furthermore, one or more means of introducing organic waste into reactor 12 can be disposed at the top, bottom and/or sides of reactor 12. In addition, organic waste can be introduced into reactor 12 continuously or intermittently.

Bottom tap 28 extends from lower portion 16 of reactor 12 and is suitable for removal of molten metal from reactor 12. Additional drains may be provided as a means of removing continuously, or discretely, additional phases. Material can also be removed by other methods, such as are known in the art.

Induction coil 30 is disposed at lower portion 16 of reactor 12 for heating molten metal bath 32 in reactor 12. It is to be understood that, alternatively, reactor 12 can be heated by other suitable means, such as by oxyfuel burners, electric arcs, plasma, etc.

Trunions 34 can be disposed at reactor 12 for manipulation of reactor 12. Seal 36 is disposed between reactor 12 and off-gas outlet 18 and is suitable for allowing partial rotation of reactor 12 about trunions 34 without breaking seal 36.

Molten metal bath 32 is disposed within reactor 12. A metal bath, as defined herein, comprises at least one metal, metal oxide, metal salt, metal alloy or metal solution, or combinations thereof. A metal solution, as defined herein, is a metal containing a dissolved non-metal component, such as carbon or sulfur.

In one embodiment, molten metal bath 32 is a low temperature bath. A low temperature bath, as defined herein, is a molten metal bath which melts at a temperature of less than about 2000° F. Suitable constituents of a low temperature bath can include, for example, aluminum, copper, zinc, etc.

In an alternate embodiment, molten metal bath 32 is a high temperature bath. A high temperature bath, as defined herein, is a molten metal bath which melts at a temperature that is greater than or equal to about 2000° F. Suitable constituents of a high temperature bath can include, for example, iron, chromium, manganese, nickel, cobalt, etc.

Molten metal bath 32 is formed by partially filling reactor 12 with a suitable metal, metal compound, metal alloy or metal solution, or combinations therein. Molten metal bath 32 is then heated to a suitable temperature by activating induction coil 30 or by other means, not shown.

Suitable operating conditions for reactor 12 include a temperature of molten metal bath 32 which is sufficient to dissociate waste, optionally containing an inorganic component, to form a gasified hydrocarbon component. The hydrocarbon component, as defined herein, can include small hydrocarbons, for example those hydrocarbons containing up to about six carbon atoms, such as methane, ethylene, butane, cyclohexane and benzene. In addition, other gaseous carbon components, such as carbon monoxide, cab also be produced. Any inorganic component of the organic waste, which can include, for example, metal, aluminate, silicate, sulfur and/or halogen, remains in the metal and/or vitreous phases or can be chemically or physically separated from the gaseous phase.

In one embodiment, the operating range temperature of molten metal bath 32 is between about 1000° F. to about 2800° F.

In another embodiment, gas stream introduction means includes tuyere 38, which is disposed at lower portion 16 of reactor 12. Tuyere 38 is dimensioned and configured for introducing a gas stream into the reactor. Tuyere 38 includes stream inlet tube 40, which provides fluid communication between stream source 42 and lower portion 16 of reactor 12 through stream inlet 44. Stream inlet 44 is disposed in lower portion 16 of reactor 12 at the end of stream inlet tube 40. It is to be understood that suitable means for introducing a gas stream into molten metal bath 32 includes tuyeres, lances, inlets and other components capable of directing a gas or gasifiable component into a molten metal bath. It is also to be understood that the means of introducing a gas stream can direct the gas stream into molten metal bath 32 through the top, bottom or sides of reactor 12. Furthermore, it is to be understood that one or more means of introducing a gas stream into molten metal bath 32 can be disposed at the top, bottom and/or sides of reactor 12.

A gas stream, as defined herein, is a stream containing at least one gaseous or gasifiable component that, when directed through molten metal bath 32, then flows in a substantially upwards direction through molten metal bath 32 and thereby molten metal in the gas stream to form fountain 46 above molten metal bath 32. Fountain 46 comprises a stream of molten drops of various sizes that are directed out of molten metal bath 32 by the gas stream.

A suitable gas stream can include a nonreactive gas, a reactive gas, and/or a second organic waste. Examples of a suitable nonreactive gas include nitrogen or argon, while a suitable reactive gas is, for example, hydrogen. Examples of organic wastes suitable for a gas stream include organic wastes wherein at least a portion of the waste, or a dissociation product of the waste, is gasifiable.

In yet another embodiment, vitreous layer 48 is disposed in reactor 12 on molten metal bath 32. Vitreous layer 48 is substantially immiscible with molten metal bath 32. Vitreous layer 48 can have a lower thermal conductivity than that of molten metal bath 32. Radiant heat loss from molten metal bath 32 can thereby be reduced to significantly below the radiant heat loss from molten bath where no vitreous layer is present.

Examples of metal oxides typically found in vitreous layer 48 include titanium oxide (TiO), zirconium oxide ($ZrO_2$), aluminum oxide ($Al_2O_3$), magnesium oxide (MgO), calcium oxide (CaO), etc. Other examples of suitable components of vitreous layer 48 include halides, sulfides, phosphates, heavy metals, etc. It is to be understood that vitreous layer 48 can include more than one metal oxide. Vitreous layer 48 is fluid and gasified hydrocarbons, carbon monoxide and other gases can pass across vitreous layer 48 from molten metal bath 32.

In one embodiment, vitreous layer 48 is formed by directing suitable components, such as metals, metal oxides, halogens, sulfur, phosphorus, heavy metals, fluxes, sludges, etc., from flux source 50 through inlet tube 52 and onto and into molten metal bath 32 or from below the surface of molten metal bath 32. The components form oxides by exposure of the components to an oxidant, not shown, directed into reactor 12 or from other stable compounds at system conditions by reacting with other less stable components, such as alkali metal or alkaline earth metal cations. Examples of such stable reacting products include calcium fluoride ($CaF_2$) and magnesium phosphate ($Mg_3(PO_4)_2$). A thin vitreous layer 48 facilitates the passage of gasified hydrocarbons, carbon monoxide and other gaseous species across vitreous layer 48 to gas layer 54.

Gas layer 54 develops over molten metal bath 32 and generally around fountain 46. Gas layer 54 typically extends from upper portion 14 of reactor 12 through off-gas outlet 18. Gas layer 54 comprises the gaseous component of the gas stream and gasified waste and/or waste decomposition products, such as smaller hydrocarbons, carbon monoxide and hydrogen.

A reaction zone within reactor 12 includes molten metal bath 32, gas layer 54 and optionally, fountain 46 and/or vitreous layer 48. A substantial portion of the reaction within reactor 12 occurs within the reaction zone.

In yet another embodiment, separating means 56 is provided to physically and/or chemically separate impurities, such as condensible components, particulates or reactive gases, from the gasified hydrocarbon. Separating means 56 are typically disposed at off-gas outlet 18. Separating means 56 are suitable to remove entrained physical impurities from a gasified component as the gasified component is directed through separating means 56. Separating means 56 are also suitable to remove chemical impurities, such as the reactive gases halogen or hydrogen halide, from a gasified component as the gasified component is directed through baffles 56. Examples of suitable separating means include baffles and calcium oxide packed beds.

Separating means 56 can be disposed upstream, downstream or in off-gas outlet 18. Additionally, separating means can include horizontal baffles, vertical baffles, centrifugal separators, cyclone separators and any other means known in the art of separating a physical impurity from a gas stream. Furthermore, separating means 56 can include any other means known in the art of separating a chemical impurity from a gas stream.

In an alternative embodiment, a means for rapidly cooling the off-gas, not shown, is provided to control chemical reactions and degradation of desirable hydrocarbons in the off-gas, as is disclosed in U.S. patent application Ser. No. 08/041,491, filed on Apr. 1, 1993, and which is commonly assigned with this patent application, the teachings of which are incorporated herein by reference.

In another embodiment, a processing unit, not shown, is provided to convert the hydrocarbons contained in the off-gas to a desirable product. A suitable processing unit, for example, includes an ethylene furnace, or an olefin furnace, which converts the hydrocarbons in the off-gas to ethylene, or olefin, respectively, by means known in the art.

Organic waste, as defined herein, contains at least one organic component wherein the organic component can be dissociated to form a gasified hydrocarbon. The organic waste can contain an inorganic component, such as a metal, halogen, sulfur, phosphorus, etc. Typical organic wastes containing an inorganic component include mixtures comprising by-products, manufacturing intermediates, off-specification products and wastes wherein the inorganic component is organically or inorganically bound. A wide variety of waste material is suitable for treatment by this invention. This waste can include organic and organometallic substances. Examples of suitable wastes include plastics, polymers, coke wastes, petroleum residuals, tires and pesticides.

In one embodiment organic waste is directed into at least one portion of the reaction zone, specifically gas layer 54, molten metal bath 32 or, optionally, fountain 46 or vitreous layer 48, by injecting the organic waste into upper portion 14 of reactor 12. The organic waste is directed from waste source 22 through lance 20 into the reaction zone through upper portion 14 of reactor 12. Upon injection of the organic waste, the organic waste gasifies, and/or is dissociated and partially gasifies, to form at least one gasified hydrocarbon component. The gasified hydrocarbon component then migrates into, or remains in, gas layer 54.

In another embodiment wherein the organic waste contains an inorganic component, the inorganic component is concurrently separated from the gasified hydrocarbon by being retained in vitreous layer 48 and/or molten metal bath 32 and/or by being subsequently removed by separating means 56. The inorganic component can include metals, which could be retained in molten metal bath 32, light metals, or vitreous agents. A vitreous agent as defined herein is a condensible material that, under the operating conditions of reactor 12, is not in its elemental form. Such agents include, for example, $SiO_2$, $Al_2O_3$, Cas, $CaF_2$, $Mg_3(PO_4)_2$, etc. The inorganic component can also contain metal salts, such as oxides, ash-forming substances, such as silicate or aluminate, sulfur and halogens which could be retained in vitreous layer 48.

In an alternate embodiment, where the waste is bulky, the waste is directed through bulk waste inlet 26 into upper portion 14 into the reaction zone in reactor 12.

The size of the hydrocarbon produced by the dissociation of the organic waste, for example a two-carbon hydrocarbon or a four-carbon hydrocarbon, can be substantially controlled by varying the operating temperature of molten metal bath 32, such as by using a high temperature bath or a low temperature bath. The hydrocarbon produced can also be effected by controlling the length of time that the organic waste, and the organic waste decomposition products are exposed to molten metal. This exposure time can be controlled, for example, by varying the location of organic waste introduction into molten metal bath 32, by changing the size of fountain 46, or by other means known in the art. Furthermore, the hydrocarbon produced can be also effected by the size of the organic waste particles that are introduced into molten metal bath 32.

In another embodiment, concurrent with the introduction of waste into reactor 12, a suitable gas stream of a gas that is nonreactive under the conditions in the reaction zone, such as nitrogen or argon, is directed from stream source 42 through gas stream inlet tube 40 into lower portion 16 of reactor 12. The gas stream then flows through molten metal bath 32, and vitreous layer 48, into gas layer 54. The gas stream entrains molten metal drops and droplets from molten metal bath 32 and thereby forms fountain 46 upon entering gas layer 54. The organic waste is then injected into gas layer 54 wherein the organic waste is contacted with fountain 46 to thereby dissociate the organic waste to form a hydrocarbon gas.

In yet another embodiment, the gas stream comprises a second organic waste which contains a gasifiable component or dissociates to form a gasifiable component. Upon introduction of the second organic waste into molten metal bath 32, the second organic waste dissociates to its atomic constituents and then the atomic constituents reformulate to produce a gasified component which then migrates through molten metal bath 32 to gas layer 54. Optionally, the type of organic waste comprising the second organic waste and/or the rate of introduction of the second organic waste into molten metal bath 32 can be controlled to form a gasified components which is sufficient to produce fountain 46.

The gasified hydrocarbon product, and other gaseous species such as carbon monoxide and hydrogen, contained in gas layer 54 are then directed out of upper portion 14 of reactor 12 through separating means 56 and off-gas outlet 18. Chemical and physical impurities, such as condensibles, for example mercury and sulfur, particulates, and reactive gases, for example halogens, entrained with the gasified hydrocarbon will then be separated from the gasified hydrocarbon.

The gasified hydrocarbon is then directed out of reactor 12 through off-gas outlet 18.

EQUIVALENTS

Those skilled in the art will recognize, or be able to ascertain using no more than routine experimentation, many equivalents to the specific embodiments of the invention described specifically herein. Such equivalents are intended to be encompassed in the scope of the claims.

What is claimed is:

1. A method for dissociating organic waste to produce a gasified hydrocarbon, comprising the steps of:
   a) forming a reaction zone in a reactor for dissociating a first organic waste to form a gasified hydrocarbon, wherein the reaction zone contains a molten metal bath and a gas layer over the molten metal bath;
   b) introducing a gas stream into said molten metal bath to form a fountain, disposed above said molten metal bath, for dissociating the first organic waste in the gas layer to form the gasified hydrocarbon;
   c) introducing the first organic waste into said gas layer, whereby the first organic waste is exposed to the fountain, thereby dissociating in the gas layer at least a portion of the first organic waste to form the gasified hydrocarbon.

2. A method of claim 1 wherein the gas stream comprises a gas which is inert under the conditions maintained in said reaction zone.

3. A method of claim 2 wherein the gas stream comprises argon.

4. A method of claim 2 wherein the gas stream comprises nitrogen.

5. A method of claim 2 wherein the gas stream comprises hydrogen.

6. A method of claim 2 wherein the gas stream comprises a second organic waste, wherein at least one component of the second organic waste is gasified within said molten metal bath.

7. A method of claim 2 further comprising the step of directing said gasified hydrocarbon through a means for removing an impurity.

8. A method of claim 2 further comprising the steps of:
   a) maintaining a cooling unit under conditions sufficient to quench dissociation of said gasified hydrocarbon; and
   b) directing said gasified hydrocarbon into said cooling unit whereby said gasified hydrocarbon is quenched.

9. A method of claim 1 wherein the molten metal bath includes a vitreous layer, which is disposed in the upper portion of the molten metal bath, for removing an impurity from the gasified hydrocarbon.

10. A method of claim 9 wherein the molten metal bath comprises iron.

11. A method for dissociating organic waste to produce ethylene, comprising the steps of:
   a) forming a reaction zone in a reactor for dissociating a first organic waste to form a gasified hydrocarbon, wherein the reaction zone contains a molten metal bath and a gas layer over the molten metal bath; and
   b) introducing a gas stream into said molten metal bath, whereby the gas stream forms a fountain, disposed above said molten metal bath, for dissociating a first organic waste in the gas layer to form a gasified hydrocarbon;
   c) introducing the first organic waste into said gas layer whereby the organic waste is exposed to said fountain and whereby at least a portion of the first organic waste dissociates in the gas layer to form said gasified hydrocarbon; and
   d) directing the gasified hydrocarbon into an ethylene furnace whereby at least a portion of the gasified hydrocarbon is converted into ethylene.

12. A method for dissociating organic waste with molten metal to produce olefin, comprising the steps of:
   a) forming a reaction zone in a reactor for dissociating a first organic waste to form a gasified hydrocarbon, wherein the reaction zone contains a molten metal bath and a gas layer over the molten metal bath; and
   b) introducing a gas stream into said molten metal bath, whereby the gas stream forms a fountain, disposed above said molten metal bath, for dissociating a first organic waste in the gas layer to form a gasified hydrocarbon;
   c) introducing the first organic waste into said gas layer whereby the organic waste is exposed to said fountain and whereby at least a portion of the first organic waste dissociates in the gas layer to form said gasified hydrocarbon; and
   d) directing the gasified hydrocarbon into an olefin furnace whereby at least a portion of the gasified hydrocarbon is converted into olefin.

13. A method for dissociating organic waste to produce a mixture of hydrocarbon and carbon monoxide gases, comprising the steps of:
   a) forming a reaction zone, containing a gas layer disposed above a molten metal bath;
   b) introducing a first organic waste into said gas layer; and
   c) introducing a second organic waste into said molten metal bath whereby the second organic waste dissociates to atomic constituents and reformulates said atomic constituents to produce carbon monoxide gas, and whereby the carbon monoxide gas forms a fountain of molten metal, disposed above said molten metal bath, which contacts said first organic waste, thereby dissociating at least a portion of the first organic waste in the gas layer to form said gasified hydrocarbon.

14. A method for dissociating organic waste to produce a hydrocarbon, comprising the steps of:
   a) forming a reaction zone, containing a gas layer disposed over a molten metal bath;
   b) introducing a first organic waste into said molten metal bath whereby the first organic waste dissociates to atomic constituents and reformulates said constituents to produce the gas stream, whereby said gas stream forms a fountain, disposed in said gas layer, for dissociating a first organic waste in the gas layer to form a gasified hydrocarbon; and
   c) introducing a second organic waste into said gas layer, whereby the second organic waste is exposed to said fountain and whereby at least a portion of the second organic waste dissociates to form said gasified hydrocarbon.

* * * * *